United States Patent
Iwasaki

(10) Patent No.: US 11,253,143 B2
(45) Date of Patent: Feb. 22, 2022

(54) ENDOSCOPE REPROCESSOR

(71) Applicant: OLYMPUS CORPORATION, Tokyo (JP)

(72) Inventor: Tomokazu Iwasaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/088,124

(22) Filed: Nov. 3, 2020

(65) Prior Publication Data

US 2021/0127962 A1    May 6, 2021

Related U.S. Application Data

(63) Continuation of application No. PCT/JP2019/010659, filed on Mar. 14, 2019.

(30) Foreign Application Priority Data

May 7, 2018    (JP) .............................. JP2018-089353

(51) Int. Cl.
*A61B 1/12*    (2006.01)
*B08B 3/08*    (2006.01)
(Continued)

(52) U.S. Cl.
CPC .............. *A61B 1/121* (2013.01); *B08B 3/08* (2013.01); *B67D 7/0294* (2013.01); *B67D 7/78* (2013.01)

(58) Field of Classification Search
CPC ....... A61B 1/12; A61B 1/015; A61B 1/00119; B08B 3/08; B67D 7/78; B67D 7/0294
(Continued)

(56) References Cited

U.S. PATENT DOCUMENTS 4,840,621 A  *  6/1989  Larkin .................. A61M 39/18
                                                        141/330
6,874,517 B2 *  4/2005  Halstead ................ A61B 1/123
                                                        134/170
(Continued)

FOREIGN PATENT DOCUMENTS

EP    2949263 A1    12/2015
EP    3078321 A1    10/2016
(Continued)

OTHER PUBLICATIONS

International Search Report dated May 21, 2010 issued in PCT/JP2019/010659.

*Primary Examiner* — Timothy L Maust
(74) *Attorney, Agent, or Firm* — Scully, Scott, Murphy & Presser, P.C.

(57) ABSTRACT

An endoscope reprocessor includes: a housing unit that houses a medicinal solution bottle such that a sealing portion is located on a top surface; a first guide that guides the housing unit such that the housing unit is capable of advancing and retreating between a first point and a second point; a movable unit that moves in cooperation with advancing of the housing unit; an unsealing member provided in the movable unit and arranged at a position higher than the sealing portion of the medicinal solution bottle housed in the housing unit at the first point, the unsealing member having a shape protruding toward the top surface at a predetermined length to pierce the sealing portion when the medicinal solution bottle reaches the second point by descending as the movable unit advances; and a second guide that guides an advancing direction of the movable unit.

9 Claims, 9 Drawing Sheets

(51) Int. Cl.
*B67D 7/02* (2010.01)
*B67D 7/78* (2010.01)

(58) Field of Classification Search
USPC .................................................. 141/284, 330
See application file for complete search history.

(56) References Cited

U.S. PATENT DOCUMENTS

| | | | |
|---|---|---|---|
| 7,476,368 B2 * | 1/2009 | Sargent | A61L 2/20 |
| | | | 422/292 |
| 7,901,349 B2 * | 3/2011 | Feld | A61L 2/18 |
| | | | 600/155 |
| 8,506,726 B2 * | 8/2013 | Cui | A61B 90/70 |
| | | | 134/56 R |
| 9,788,711 B2 * | 10/2017 | Ogawa | B08B 9/023 |
| 9,968,246 B2 * | 5/2018 | Iwanami | B08B 3/108 |
| 10,194,790 B2 * | 2/2019 | Iwanaga | A61B 1/12 |
| 10,561,307 B2 * | 2/2020 | Nguyen | A61B 1/00119 |
| 2008/0267812 A1 * | 10/2008 | Kawachi | A61B 1/123 |
| | | | 422/3 |
| 2016/0135667 A1 * | 5/2016 | Takazawa | A61B 1/00128 |
| | | | 134/166 C |
| 2016/0249794 A1 * | 9/2016 | Suzuki | C02F 1/001 |
| | | | 134/169 C |
| 2016/0309989 A1 * | 10/2016 | Sato | A61B 1/12 |
| 2021/0127962 A1 * | 5/2021 | Iwasaki | B67D 7/0294 |

FOREIGN PATENT DOCUMENTS

| | | |
|---|---|---|
| JP | 2009-148315 A | 7/2009 |
| WO | WO 2015/104872 A1 | 7/2015 |
| WO | WO 2016/080074 A1 | 5/2016 |

\* cited by examiner

ENDOSCOPE REPROCESSOR

CROSS REFERENCE TO RELATED APPLICATION

This application is a continuation application of PCT/JP2019/010659 filed on Mar. 14, 2019 and claims benefit of Japanese Application No. 2018-089353 filed in Japan on May 7, 2018, the entire contents of which are incorporated herein by this reference.

BACKGROUND OF THE INVENTION

1. Field of the Invention

The present invention relates to an endoscope reprocessor.

2. Description of the Related Art

Conventionally, an endoscope reprocessor has been known that uses a medicinal solution supplied by a medicinal solution supply mechanism to perform reprocessing such as cleaning/disinfecting of an endoscope.

For example, Japanese Patent Application Laid-Open Publication No. 2009-148315 discloses an endoscope cleaning apparatus that includes a bottle tray slidably disposed along a rail inclined downward toward an opening portion, in a bottle housing portion, houses a bottle in the bottle tray pulled out from the opening portion, and sets a medicinal solution bottle by pushing the bottle tray diagonally upward.

SUMMARY OF THE INVENTION

An endoscope reprocessor according to an aspect of the present invention includes: a housing unit that houses a medicinal solution bottle such that a sealing portion is located on a top surface; a first guide that guides the housing unit such that the housing unit is capable of advancing and retreating between a first point and a second point; a movable unit that moves in cooperation with advancing of the housing unit; an unsealing member provided in the movable unit and arranged at a position higher than the sealing portion of the medicinal solution bottle housed in the housing unit at the first point, the unsealing member having a shape protruding toward the top surface at a predetermined length to pierce the sealing portion when the medicinal solution bottle reaches the second point by descending as the movable unit advances; and a second guide that guides an advancing direction of the movable unit.

DETAILED DESCRIPTION OF THE PREFERRED EMBODIMENT

An embodiment of the present invention will be described below with reference to the drawings.

(Configuration)

Figure 1:
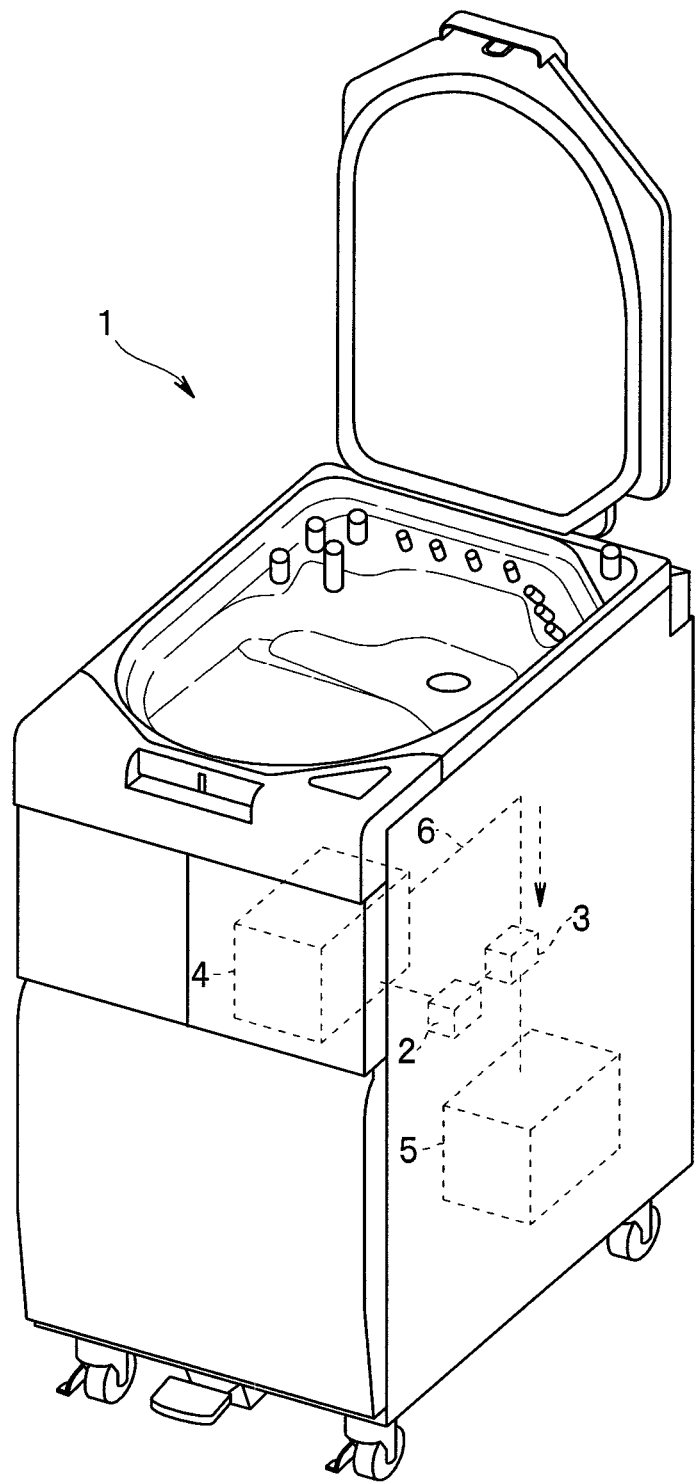
FIG. 1 is a perspective view showing an example of an endoscope reprocessor according to an embodiment of the present invention.

FIG. 1 is a perspective view showing an example of an endoscope reprocessor 1 according to the embodiment of the present invention.

The endoscope reprocessor 1 is an apparatus that performs reprocessing on a contaminated endoscope and components or accessories of the endoscope. The reprocessing in the present invention is not particularly limited, but may include rinsing with water, cleaning for removing dirt such as organic substances, disinfection for making specific microorganisms ineffectual, and sterilization for expelling or killing all microorganisms, or any combination of these. The accessories are not particularly limited, and include a suction button, an air/water feeding button, or a distal end cover that covers a distal end portion of the endoscope, for example. Such accessories are attached to the endoscope during use, and are removed from the endoscope during reprocessing.

The endoscope reprocessor 1 includes a control unit 2, a pump 3, a medicinal solution supply mechanism 4, a medicinal solution tank 5, and a connection tube 6.

The control unit 2 includes a processor and a memory, and is connected to respective units provided in the endoscope reprocessor 1, for example, the pump 3 and the medicinal solution supply mechanism 4. The control unit 2 controls the respective units in the endoscope reprocessor 1 by processing of the processor.

The medicinal solution supply mechanism 4 and the medicinal solution tank 5 are connected to each other by the connection tube 6. When the pump 3 is driven by the control of the control unit 2, the medicinal solution supply mechanism 4 supplies a medicinal solution to be used in the reprocessing to the medicinal solution tank 5 via the connection tube 6. The medicinal solution is, for example, a disinfection solution containing peracetic acid.

Figure 2:
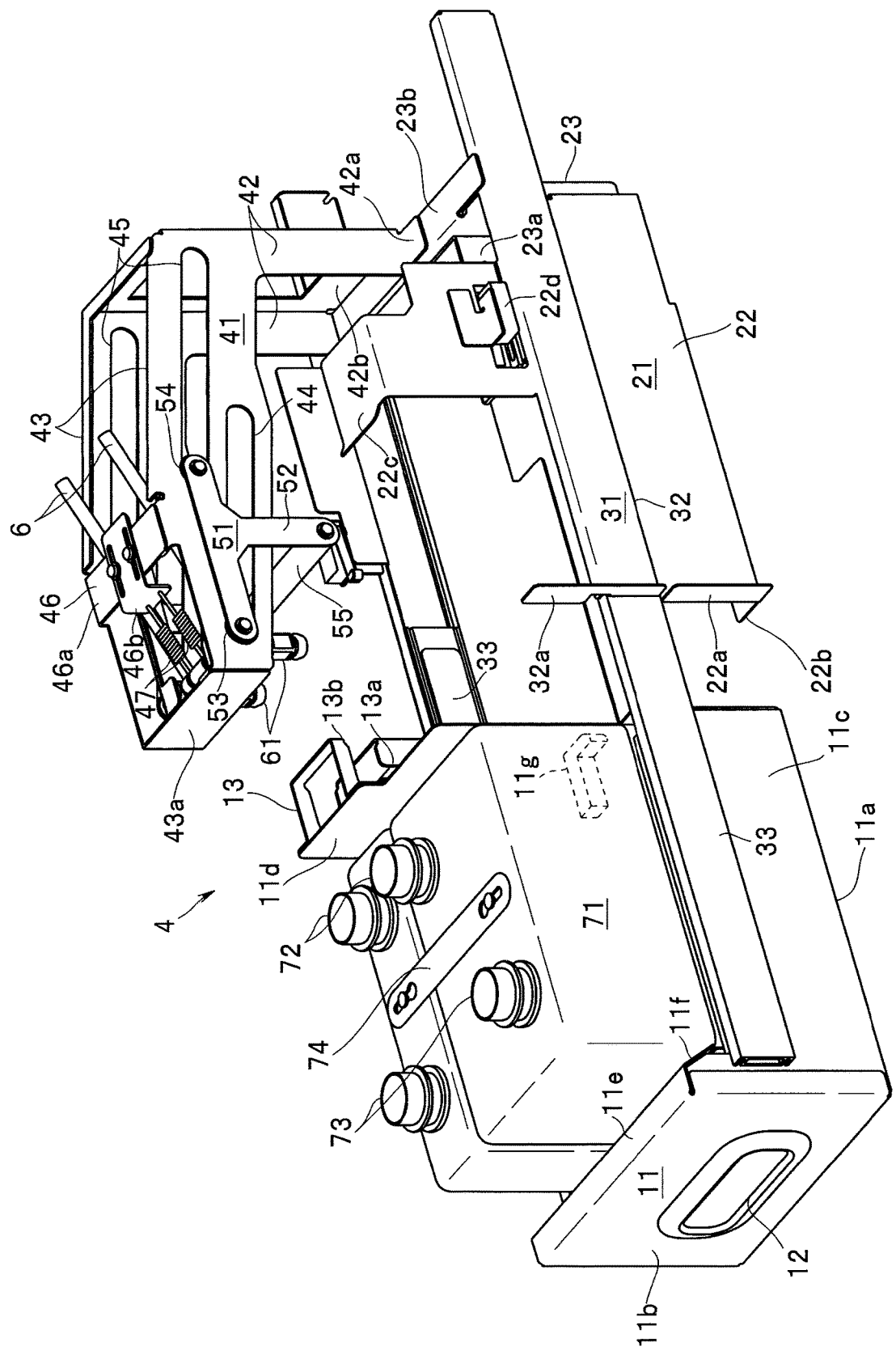
FIG. 2 is a perspective view showing an example of a medicinal solution supply mechanism of the endoscope reprocessor according to the embodiment of the present invention.
Figure 3:
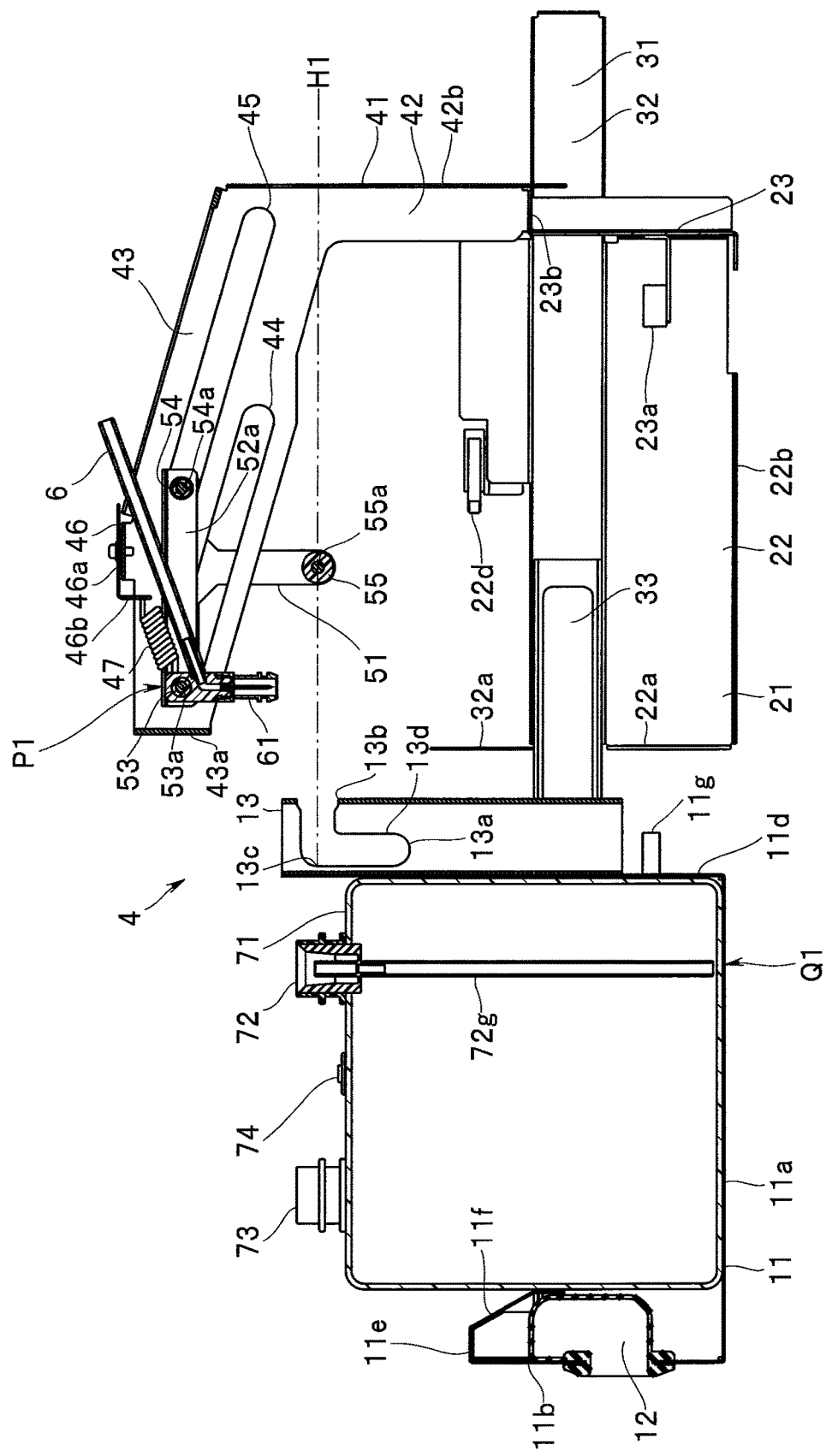
FIG. 3 is a cross-sectional view of the medicinal solution supply mechanism of the endoscope reprocessor according to the embodiment of the present invention.

FIG. 2 is a perspective view showing an example of the medicinal solution supply mechanism 4 of the endoscope reprocessor 1 according to the embodiment of the present invention. FIG. 3 is a cross-sectional view of the medicinal solution supply mechanism 4 of the endoscope reprocessor 1 according to the embodiment of the present invention.

As shown in FIG. 2, the medicinal solution supply mechanism 4 includes a housing portion 11 as a housing unit, a main body portion 21 as a main body, a first guide portion 31 as a first guide, a second guide portion 41 as a second guide, a movable portion 51 as a movable unit, an unsealing portion 61 as an unsealing member, and a medicinal solution bottle 71.

The housing portion 11 is made of a material such as metal, and houses the medicinal solution bottle 71 such that a sealing portion 72 of the medicinal solution bottle 71 is located on a top surface. The housing portion 11 has a box shape with an upper part opened. The housing portion 11 includes a bottom plate 11a and a front side plate 11b, both left and right side plates 11c, and a rear side plate 11d which are continuously provided to rise from the bottom plate 11a. The both left and right side plates 11c are continuously provided on both left and right sides of the housing portion 11 to be adjacent to each of the front side plate 11b and the rear side plate 11d. The housing portion 11 includes an extension plate 11e extending rearward from an upper side of the front side plate 11b and a tapered guide plate 1 if inclined toward a rear side from the extension plate 11e to approach the bottom plate 11a. The tapered guide plate 1 if guides the medicinal solution bottle 71, which is inserted from above, to an appropriate housing position. A hook 11g is continuously provided on a rear surface of the rear side plate 11d. The housing portion 11 includes a finger hooking portion 12 and a roller receiving portion 13.

The finger hooking portion 12 is made of a material such as rubber, and is configured such that a finger inserted through an opening can be hung. As shown in FIG. 3, the finger hooking portion 12 is provided to be recessed in the opening at a center of the front side plate 11b, is arranged below the extension plate 11e and the tapered guide plate 11f, and has a shape in which a back side is bent into a substantially L-shape.

The roller receiving portion 13 is made of a material such as metal. The roller receiving portion 13 is continuously provided on a rear surface of the rear side plate 11d. The roller receiving portion 13 has, for example, a tubular shape arranged in a vertical direction, and includes an engaging groove 13a that engages with an engaging roller 55 of the movable portion 51. On a rear surface of the roller receiving portion 13, an engaging groove opening 13b is provided at a position corresponding to a first height H1 of the engaging roller 55 such that the engaging roller 55 can enter. The engaging groove 13a has substantially an L-shape, extends forward from the engaging groove opening 13b such that both left and right side surfaces are cut out, and then extends downward. A lower end part of the engaging groove 13a is provided at a position corresponding to a second height H2 of the engaging roller 55.

The first height H1 is a height of the engaging roller 55 when the movable portion 51 is arranged at a first position P1. The second height H2 is a height of the engaging roller 55 when the movable portion 51 is arranged at a second position P2 behind the first position P1. The first height H1, the second height H2, the first position P1, and the second position P2 are set in advance.

The main body portion 21 is made of a material such as metal. The main body portion 21 is provided behind the housing portion 11. The main body portion 21 has substantially a U-shape, and includes both left and right side parts 22 and a rear part 23 continuously provided between the both left and right side parts 22. The housing portion 11 is set inside the main body portion 21.

On a front side of the both left and right side parts 22, an attachment piece 22a is continuously provided outward and is attached to an inner wall of the endoscope reprocessor 1. On a lower side of the both left and right side parts 22, a support piece 22b is continuously provided inward to support the housed housing portion 11. On an upper side of the both left and right side parts 22, a pressing piece 22c is continuously provided inward to prevent floating of the medicinal solution bottle 71 housed in the housing portion 11. On an inner side of the both left and right side parts 22, a bottle detection sensor 22d is provided.

The bottle detection sensor 22d is configured by a limit switch, for example. The bottle detection sensor 22d is connected to the control unit 2. When the medicinal solution bottle 71 housed in the housing portion 11 hits on the switch, the bottle detection sensor 22d outputs a control signal indicating that the medicinal solution bottle 71 is set, to the control unit 2. The bottle detection sensor 22d is not limited to the limit switch, and may be configured by other sensors.

A lock portion 23a is provided on a front surface of the rear part 23. The lock portion 23a performs positioning and locking of the housing portion 11. More specifically, the lock portion 23a is pressed against the rear side plate 11d of the housing portion 11 entered the main body portion 21 to perform positioning in an advancing/retreating direction of the housing portion 11. In addition, the lock portion 23a locks the hook 11g of the pressed housing portion 11, and locks the housing portion 11 not to fall off. The lock portion 23a may include a drive apparatus such as a motor, and the hook 11g may be released by driving of the motor under the control of the control unit 2 to release the lock.

A bottle remaining amount sensor may be provided inside the rear part 23. The bottle remaining amount sensor is configured by, for example, a capacitive sensor capable of detecting a level of the medicinal solution remaining in the medicinal solution bottle 71. The bottle remaining amount sensor is connected to the control unit 2, and outputs a detection result to the control unit 2. On an upper side of the rear part 23, a second guide attaching plate 23b is continuously provided rearward.

The first guide portion 31 is made of metal, for example. The first guide portion 31 is continuously provided in the advancing/retreating direction of the housing portion 11 to face each of the both left and right side parts 22. The first guide portion 31 includes a guide rail 32 and a movable rail 33. On a front side of the guide rail 32, an attachment piece 32a is continuously provided outward and is attached to the inner wall of the endoscope reprocessor 1. The movable rail 33 is provided to be slidable in a longitudinal direction of the guide rail 32, and is coupled to an outer surface of each of the both left and right side plates 11c.

The housing portion 11 is guided by the first guide portion 31 to be capable of advancing and retreating between a first point Q1 and a second point Q2. The first point Q1 is a point where the housing portion 11 exiting from the main body portion 21 is arranged. The second point Q2 is a point where the housing portion 11 entering the main body portion 21 is arranged. The first point Q1 and the second point Q2 are set in advance.

In other words, the main body portion 21 is coupled to the housing portion 11 by the first guide portion 31 and is coupled to the movable portion 51 by the second guide portion 41, and the housing portion 11 is arranged in the main body portion 21 at the second point Q2.

The second guide portion 41 is made of metal, for example. The second guide portion 41 includes support plates 42, guide plates 43, a first guide hole 44, a second guide hole 45, and an urging member coupling portion 46.

The support plates 42 are erected above the main body portion 21 to face each other on both the left and right sides, and support the guide plates 43. A base end attaching plate 42a extends outward in a left-right direction on each of base end sides of the support plates 42. The base end attaching plate 42a is attached to the second guide attaching plate 23b. The respective support plates 42 are coupled to each other and reinforced by a rear reinforcing plate 42b continuously provided on a rear side.

The guide plates 43 are arranged parallel to each other from respective upper parts of the support plates 42, and extends to be inclined upward toward the front. The respective guide plates 43 are coupled to each other and reinforced by a front reinforcing plate 43a which is continuously provided on a front side. Each of the guide plates 43 includes the first guide hole 44 and the second guide hole 45 that support the movable portion 51. In other words, the second guide portion 41 includes the guide plates 43 inclined toward the main body portion 21 from the housing portion 11 to approach the main body portion 21.

The first guide hole 44 is provided in front of the second guide hole 45. The first guide hole 44 and the second guide hole 45 have an elongated shape, and are arranged parallel to each other in an extending direction of the guide plate 43.

The urging member coupling portion 46 includes a base table 46a continuously provided between the respective guide plates 43 and a coupling plate 46b that can be positioned in a front-rear direction by sliding on the base table 46a. An urging member 47 includes one end coupled to the coupling plate 46b and the other end coupled to a shaft 53a. The urging member 47 urges the movable portion 51, which is provided at the second position P2, in a direction of the first position P1. The urging member 47 is configured by, for example, a spring or an elastomer. A tension spring can be used as an example of the spring.

The movable portion 51 includes movable plates 52, a first guide roller 53, a second guide roller 54, and an engaging roller 55.

The movable plates 52 are made of metal, for example. Two movable plates 52 are provided on left and right outer sides of the guide plates 43, which are provided on the both left and right sides, to face each other. Each of the movable plates 52 has substantially a T-shape, and includes a horizontal plate extending in the front-rear direction and a vertical plate extending downward from the horizontal plate. The movable plates 52 are respectively reinforced by reinforcing plates 52a provided to face each other with the guide plates 43 interposed therebetween.

Positions, directions, and lengths of the first guide hole 44 and the second guide hole 45 in the guide plate 43 and lengths of the horizontal plate and the vertical plate in the movable plate 52 are adjusted and set in advance such that the engaging roller 55 is arranged at the first height H1 when the movable plate 52 is at the first position P1 and the engaging roller 55 is arranged at the second height H2 when the movable plate 52 is at the second position P2.

The first guide roller 53, the second guide roller 54, and the engaging roller 55 are made of resin, for example.

The first guide roller 53 is rotatably provided outside in a radial direction of the shaft 53a through which front end parts of the horizontal plates are coupled to each other to hit an inner edge of the first guide hole 44.

The second guide roller 54 is rotatably provided outside in a radial direction of a shaft 54a through which rear end parts of the horizontal plates are coupled to each other to hit an inner edge of the second guide hole 45.

The engaging roller 55 is rotatably provided outside in a radial direction of a shaft 55a through which lower end parts of the vertical plates are coupled to each other.

In other words, the housing portion 11 includes the engaging groove 13a having the engaging groove opening 13b at the position of the first height H1 on the main body portion 21. The movable portion 51 includes the engaging roller 55 arranged at the position of the first height H1 at the first point Q1 and arranged at the position of the second height H2 lower than the first height H1 at the second point Q2, and the engaging roller 55 enters the engaging groove 13a from the engaging groove opening 13b when the housing portion 11 advances from the first point Q1 to the second point Q2, and power to slide the movable portion 51 is transmitted to the engaging roller 55 from an inner edge of the engaging groove 13a. The movable portion 51 moves in cooperation with the advancing of the housing portion 11.

Figure 4:
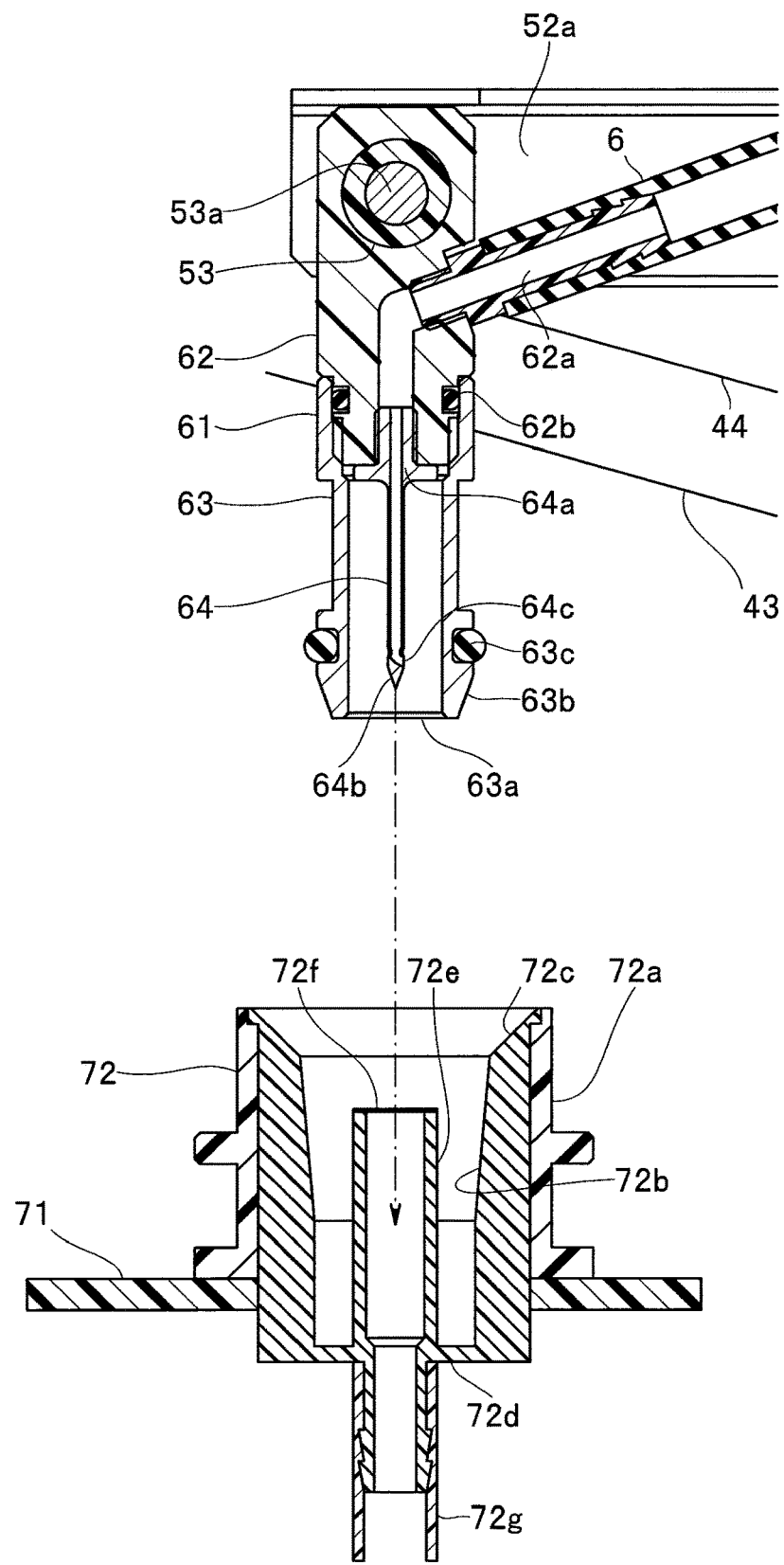
FIG. 4 is an enlarged cross-sectional view of an unsealing portion of the medicinal solution supply mechanism of the endoscope reprocessor and a sealing portion of a medicinal solution bottle according to the embodiment of the present invention.

FIG. 4 is an enlarged cross-sectional view of the unsealing portion 61 of the medicinal solution supply mechanism 4 of the endoscope reprocessor 1 and the sealing portion 72 of the medicinal solution bottle 71 according to the embodiment of the present invention.

The unsealing portion 61 is provided in the movable portion 51 at a position corresponding to the sealing portion 72 of the medicinal solution bottle 71. When a plurality of sealing portions 72 are provided, a plurality of unsealing portions 61 may also be provided. In the example of the embodiment, the sealing portion 72 is provided in each of the two medicinal solution bottles 71, and two unsealing portions 61 are also provided corresponding to the positions of the sealing portions 72. The respective medicinal solutions sucked from the respective two medicinal solution bottles 71 are supplied to the medicinal solution tank 5 to be mixed.

As shown in FIG. 4, the unsealing portion 61 descends together with the movable portion 51 and opens the medicinal solution bottle 71 by puncturing. The unsealing portion 61 includes a coupling instrument 62, a bottle mounting cylinder 63, and a puncture needle 64.

The coupling instrument 62 is made of a material such as metal. The coupling instrument 62 is rotatably suspended from the first guide roller 53 between the respective guide plates 43 such that a lower end part faces downward due to gravity. A tube mounting cylinder 62a having a slip-prevention protrusion is provided on an outer peripheral surface of the coupling instrument 62 to protrude. The connection tube 6 is mounted on the tube mounting cylinder 62a. An O-ring 62b is mounted on an outer periphery of a lower end part of the coupling instrument 62 to airtightly seal the inside of the bottle mounting cylinder 63. At the lower end part of the coupling instrument 62, an opening is provided to communicate with the tube mounting cylinder 62a through an internal flow path. When a plurality of coupling instruments 62 are provided, spacers for position adjustment may be provided among the respective coupling instruments 62.

The bottle mounting cylinder 63 is made of a material such as metal. The bottle mounting cylinder 63 is attached to the outer peripheral surface of the lower end part of the coupling instrument 62. A mounting port 63a is provided at a lower end part of the bottle mounting cylinder 63. On an outer periphery of the lower end part of the bottle mounting cylinder 63, a mounting cylinder tapered surface 63b is provided that reduces in diameter toward a lower side. An O-ring 63c is mounted above the mounting cylinder tapered surface 63b to airtightly seal the inside of the bottle mounting cylinder 63.

The puncture needle 64 is made of a material such as metal. The puncture needle 64 is provided inside the bottle mounting cylinder 63. The puncture needle 64 includes an internal flow path that causes a horizontal hole 64c provided on an outer peripheral surface of a needle tip part 64b to communicate with an opening provided in a needle base part 64a. The needle base part 64a of the puncture needle 64 is internally fitted into the opening of the coupling instrument 62 such that the needle tip part 64b faces the mounting port 63a. When the needle base part 64a of the puncture needle 64 is internally fitted into the opening of the coupling instrument 62, the internal flow path of the coupling instrument 62 communicates with the internal flow path of the puncture needle.

In other words, the unsealing portion 61 is provided in the movable portion 51 and arranged at a position higher than the sealing portion 72 of the medicinal solution bottle 71 housed in the housing portion 11 at the first point Q1, the unsealing portion 61 having a shape protruding toward the top surface at a predetermined length to pierce the sealing portion 72 when the medicinal solution bottle 71 reaches the second point Q2 by sliding down as the movable portion 51 advances.

The medicinal solution bottle 71 is made of a material such as metal or resin. The medicinal solution bottle 71 has a rectangular box shape to store the medicinal solution therein and to be housed in the housing portion 11. The medicinal solution bottle 71 includes a sealing portion 72, an intake port 73, and a fixture 74.

The sealing portion 72 includes a mouth part 72a, an outer cylinder 72b, a tapered surface 72c of the sealing portion 72, a bottom wall 72d, an inner cylinder 72e, a seal 72f, and a suction tube 72g. The mouth part 72a protrudes from the top surface of the medicinal solution bottle 71. In other words, the medicinal solution bottle 71 includes the sealing portion 72 on the top surface. The sealing portion 72 is arranged at a position where the unsealing portion 61 is mounted when the medicinal solution bottle 71 is located at the second point Q2. The outer cylinder 72b is continuously provided on an inner peripheral surface of the mouth part 72a. On an inner edge of an upper end part of the outer cylinder 72b, the sealing tapered surface 72c is provided that reduces in diameter toward the lower side and guides the mounting port 63a. The bottom wall 72d extends inward from a lower end of the outer cylinder 72b. The inner cylinder 72e is continuously provided inside the bottom wall 72d to be coaxial with the outer cylinder 72b. An upper end part and a lower end part of the inner cylinder 72e communicate with each other through the internal flow path. The seal 72f is made of, for example, a silicon film, and seals the upper end part of the inner cylinder 72e. On the outer periphery of the lower end part of the inner cylinder 72e, a slip-prevention protrusion is provided, and the suction tube 72g is mounted. When the puncture needle 64 is pierced beyond a predetermined opening force, the seal 72f is opened.

The intake port 73 is made of, for example, a waterproof/moisture-permeable sheet through which the medicinal solution in the medicinal solution bottle 71 does not leak, but air is taken in when the medicinal solution is sucked from the sealing portion 72.

When a plurality of medicinal solution bottles 71 are provided, the fixture 74 causes the medicinal solution bottles 71 to fix to each other. More specifically, the fixture 74 has an elongated band shape in which locking holes are arranged at both end parts, and causes the medicinal solution bottles 71 to fix to each other in such a manner that the locking hole arranged at one end part is hung on a locking protrusion of one medicinal solution bottle 71 and the locking hole arranged at the other end part is hung on a locking protrusion of the other medicinal solution bottle 71. A user can grasp the fixture 74 to which the medicinal solution bottle 71 is fixed, and lift the medicinal solution bottle 71.

(Operation)

Subsequently, an operation of the medicinal solution supply mechanism 4 of the endoscope reprocessor 1 will be described.

Figure 5:
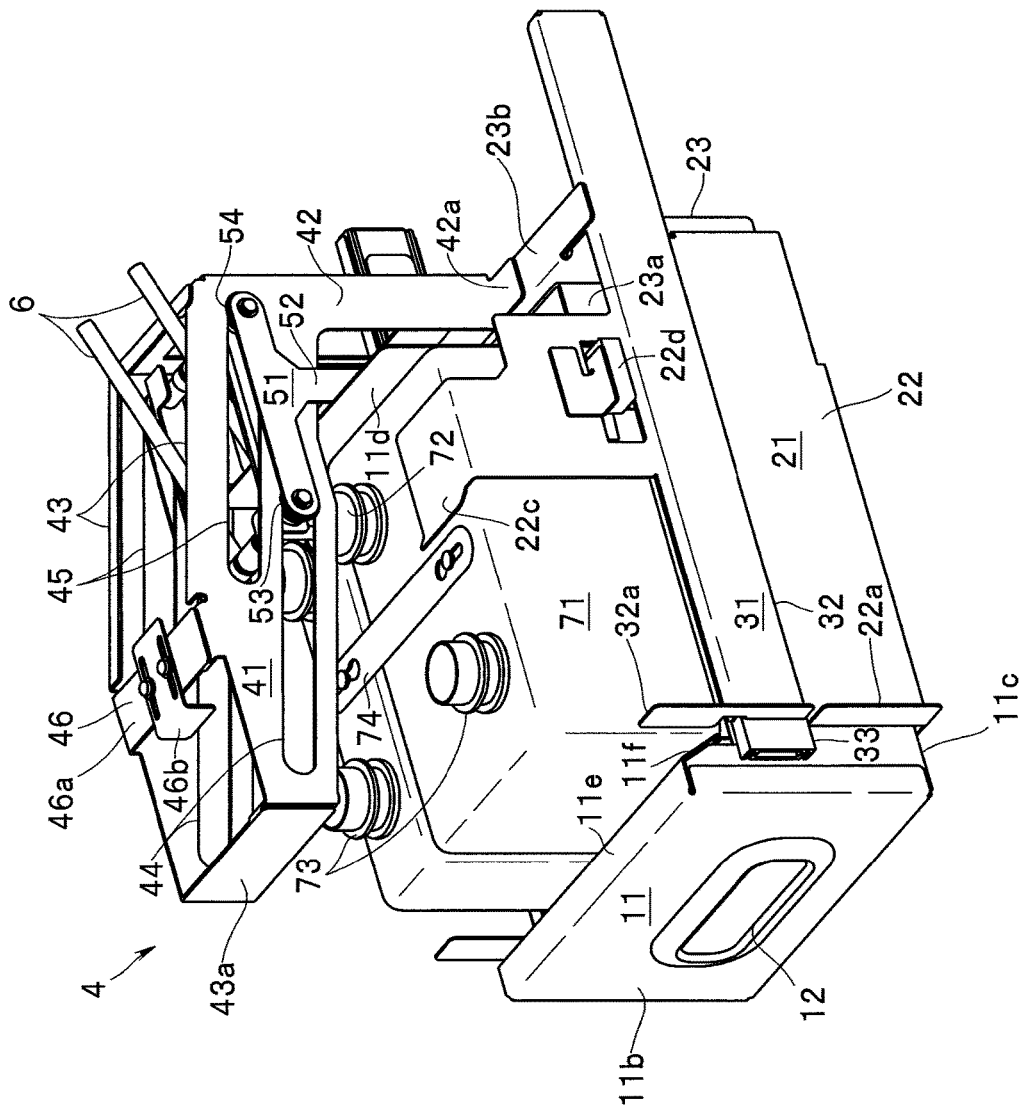
FIG. 5 is a front perspective view showing a state where a housing portion is set in a main body portion in the medicinal solution supply mechanism of the endoscope reprocessor according to the embodiment of the present invention.
Figure 6:
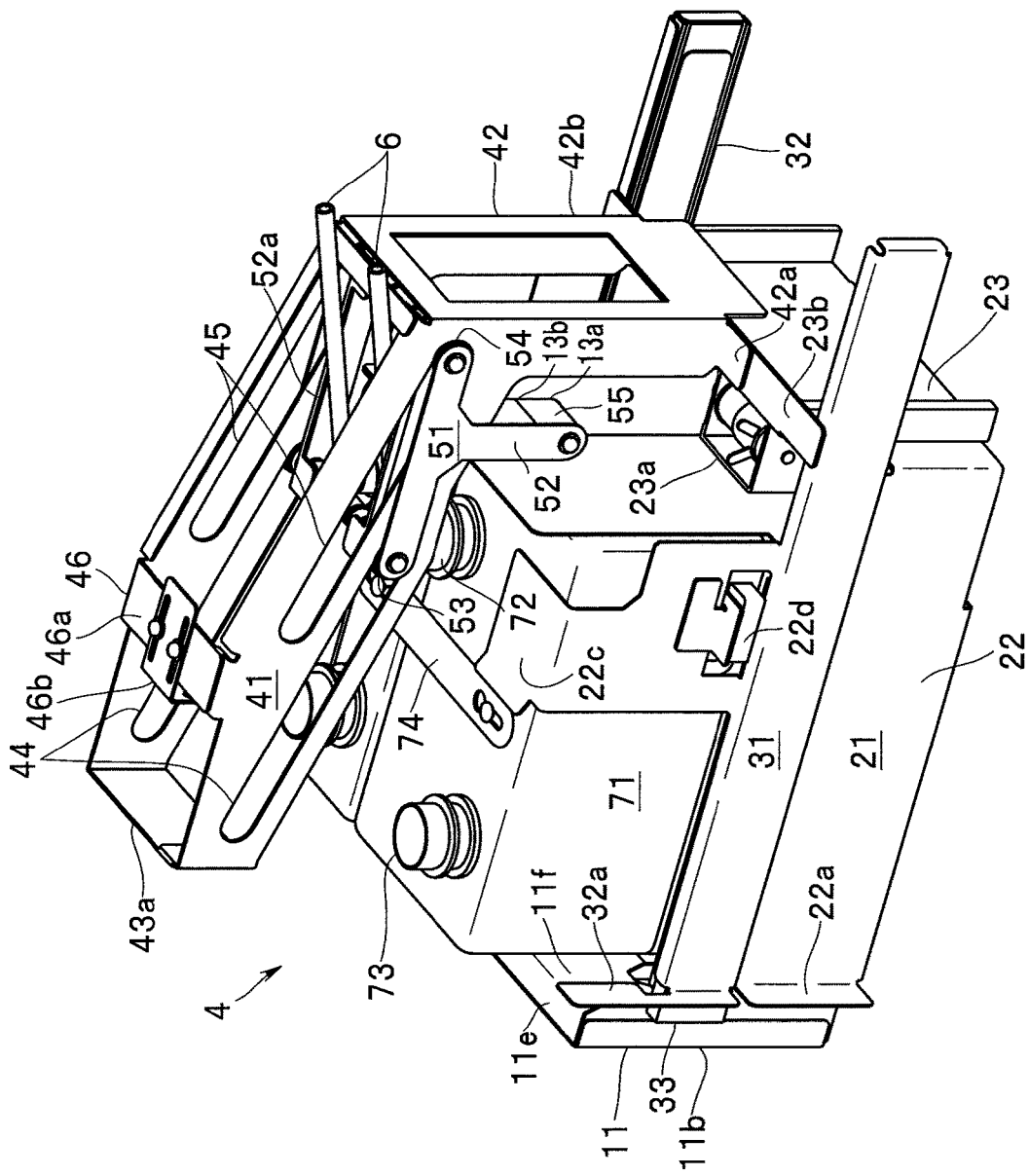
FIG. 6 is a rear perspective view showing the state where the housing portion is set in the main body portion in the medicinal solution supply mechanism of the endoscope reprocessor according to the embodiment of the present invention.
Figure 7:
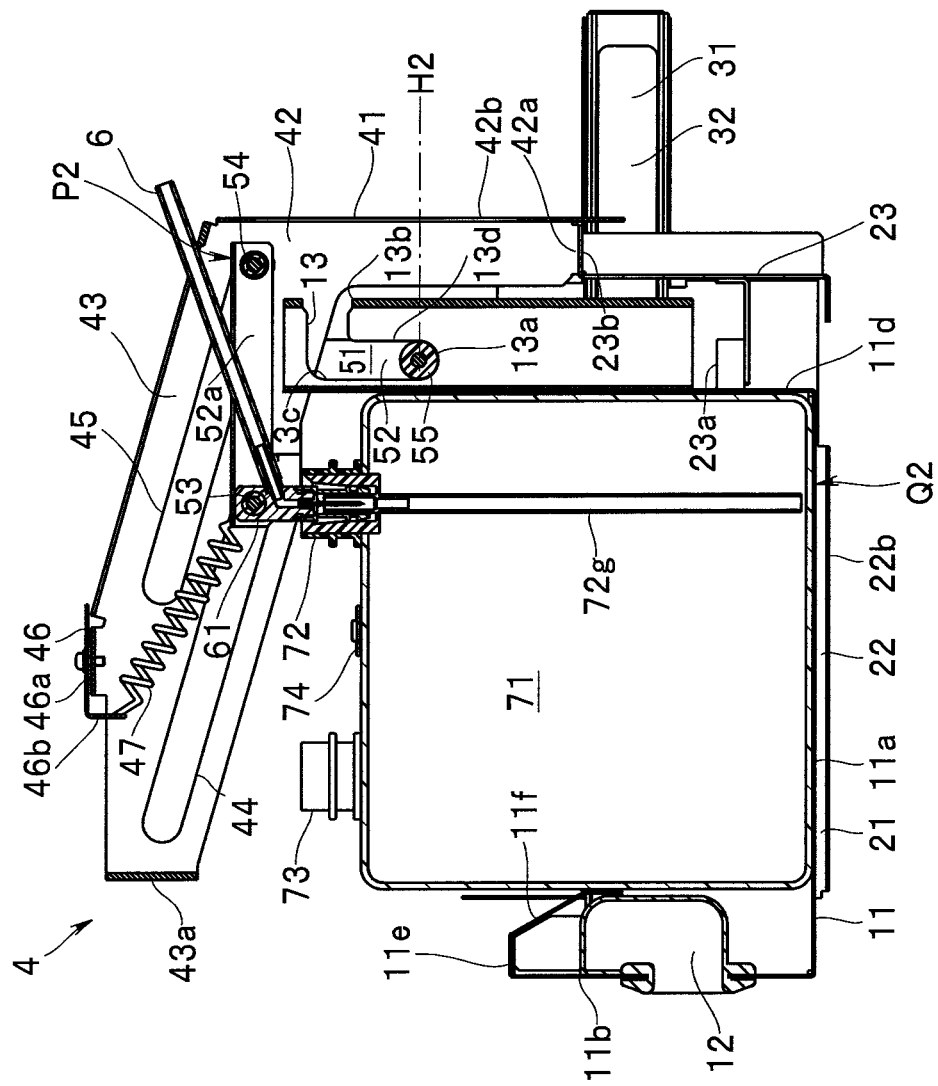
FIG. 7 is a cross-sectional view showing the state where the housing portion is set in the main body portion in the medicinal solution supply mechanism of the endoscope reprocessor according to the embodiment of the present invention.
Figure 8:
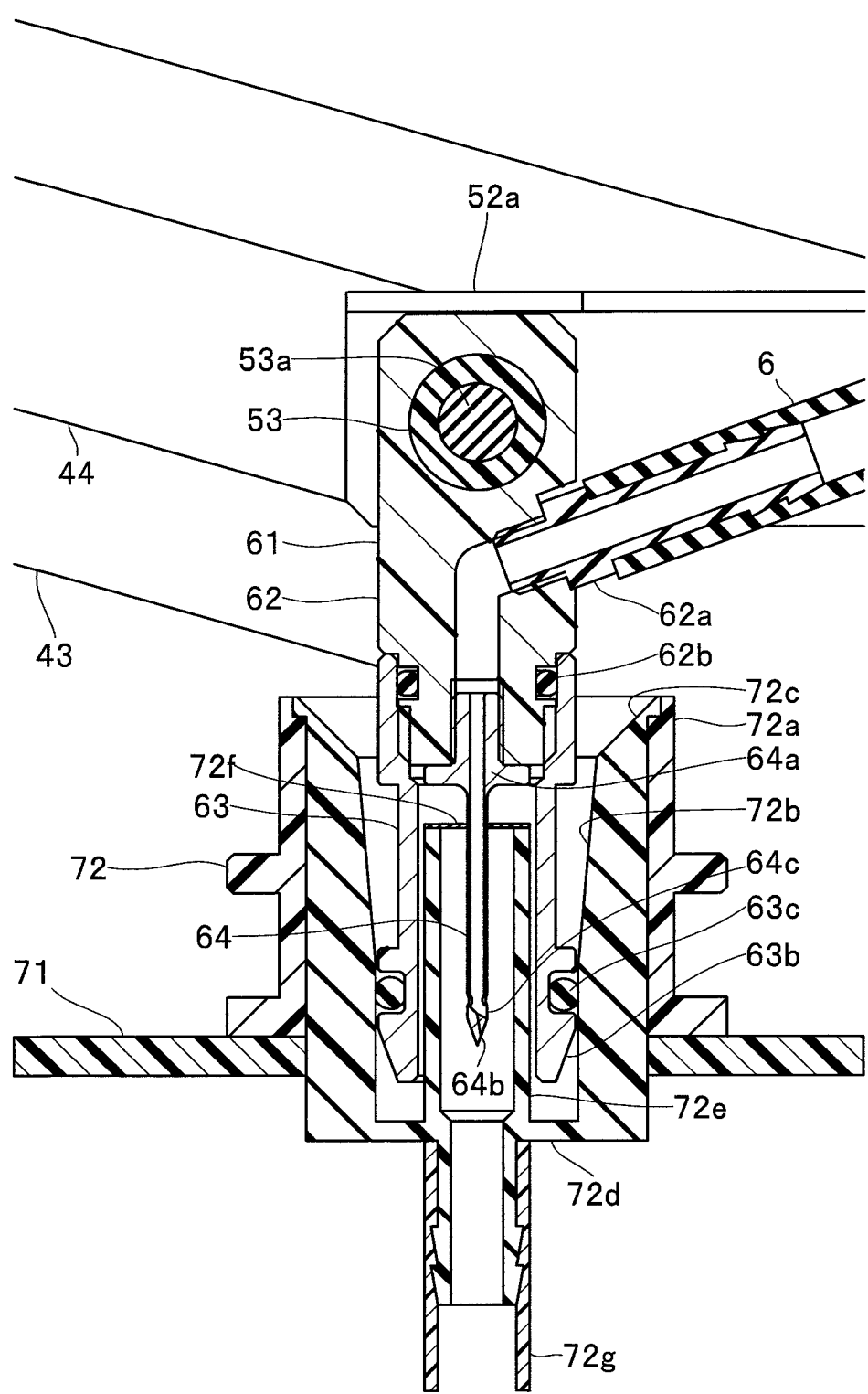
FIG. 8 is an enlarged cross-sectional view showing a state where the unsealing portion is mounted on the sealing portion of the medicinal solution bottle in the medicinal solution supply mechanism of the endoscope reprocessor according to the embodiment of the present invention.

FIGS. 5 to 8 are views showing a state where the housing portion 11 is set in the main body portion 21 in the medicinal solution supply mechanism 4 of the endoscope reprocessor 1 according to the embodiment of the present invention. FIG. 5 is a front perspective view, FIG. 6 is a rear perspective view, FIG. 7 is a cross-sectional view, and FIG. 8 is an enlarged cross-sectional view showing a state where the unsealing portion 61 is mounted on the sealing portion 72 of the medicinal solution bottle 71.

First, an operation of setting the medicinal solution bottle 71 of the medicinal solution supply mechanism 4 will be described.

When the medicinal solution bottle 71 is set or removed, the housing portion 11 is arranged at the first point Q1 and the movable portion 51 is arranged at the first position P1. The engaging roller 55 is arranged at the first height H1 when the movable portion 51 is arranged at the first position P1.

The user causes the medicinal solution bottle 71 to be housed in the housing portion 11. When the user pushes the housing portion 11 with fingers, the housing portion 11 advances toward the main body portion 21 along the first guide portion 31.

When the housing portion 11 advances, the engaging roller 55 enters the engaging groove 13a from the engaging groove opening 13b. When the engaging roller 55 hits on a front edge 13c of the engaging groove 13a, power is transmitted to the engaging roller 55 from the front edge 13c, and the movable portion 51 slides diagonally downward along the second guide portion 41 against the urging force of the urging member 47.

When the movable portion 51 slides diagonally downward, the unsealing portion 61 also descends toward the medicinal solution bottle 71. When the unsealing portion 61 descends, the bottle mounting cylinder 63 is inserted into the sealing portion 72 such that a cylinder wall is housed between the outer cylinder 72b and the inner cylinder 72e. When the inner cylinder 72e is inserted into the bottle mounting cylinder 63 from the mounting port 63a, the puncture needle 64 pierces and punctures the seal 72f. When the seal 72f is punctured, the medicinal solution bottle 71 and the connection tube 6 communicate with each other.

As shown in FIGS. 5 to 8, when the housing portion 11 is set in the main body portion 21, the movable portion 51 is arranged at the second position P2 and the engaging roller 55 is arranged at the second height H2. The movable portion 51 is urged in the direction of the first position P1 by the urging member 47, but the housing portion 11 is positioned at the second point Q2 when the housing portion 11 is pressed against the lock portion 23a. The lock portion 23a locks the hook 11g of the housing portion 11, and locks the housing portion 11 not to fall off.

Next, the operation of removing the medicinal solution bottle 71 will be described.

The control unit 2 outputs a control signal to the lock portion 23a to release the lock of the housing portion 11. The user hangs fingers on the finger hooking portion 12 and pulls the housing portion 11 forward. The housing portion 11 retreats from the main body portion 21 along the first guide portion 31. When the engaging roller 55 hits on a rear edge 13d of the engaging groove 13a, power is transmitted to the engaging roller 55 from the rear edge 13d. In addition, since the urging force of the urging member 47 is applied to the movable portion 51, the movable portion 51 slides diagonally upward along the first guide portion 31.

When the movable portion 51 slides diagonally upward, the unsealing portion 61 also ascends. However, at this time, since the floating of the medicinal solution bottle 71 is restricted by the pressing piece 22c, the unsealing portion 61 is removed from the sealing portion 72.

When the housing portion 11 reaches the first point Q1, the movable portion 51 is arranged at the first position P1 and the engaging roller 55 is arranged at the first height H1.

Subsequently, a relation between the pushing force of the user and the opening force of the unsealing portion 61 will be described.

Figure 9:
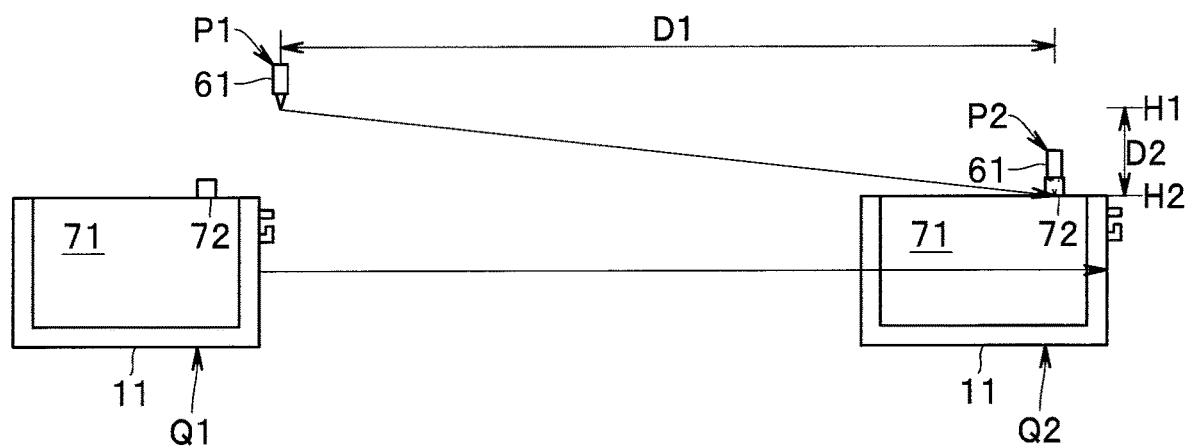
FIG. 9 is an explanatory diagram illustrating a pushing force of a user and an opening force of the unsealing portion in the medicinal solution supply mechanism of the endoscope reprocessor according to the embodiment of the present invention.

FIG. 9 is an explanatory diagram illustrating the pushing force of the user and the opening force of the unsealing portion 61 in the medicinal solution supply mechanism 4 of the endoscope reprocessor 1 according to the embodiment of the present invention.

The pushing force of the user against the housing portion 11 is transmitted to the movable portion 51, and the unsealing portion 61 descends by the movable portion 51. As shown in FIG. 9, in the medicinal solution supply mechanism 4, a horizontal distance component D1 included in a movement path of the unsealing portion 61 is set to be longer than a vertical distance component D2. The opening force for opening the unsealing portion 61 is increased as much as the vertical distance component D2 is shorter than the horizontal distance component D1.

In other words, the second guide portion 41 guides the advancing direction of the movable portion 51 such that a height difference of the descent of the unsealing portion 61 is smaller than the moving distance of the housing portion 11. Thus, in the medicinal solution supply mechanism 4, the housing portion 11 housing the medicinal solution bottle 71 can be set in the main body portion 21 with a smaller force.

According to the embodiment, the endoscope reprocessor 1 can set the medicinal solution bottle 71 in the medicinal solution supply mechanism 4 with a smaller force, and the work load on the user can be reduced.

The example is described in the embodiment in which the medicinal solution is a disinfection solution containing peracetic acid, but the present invention is not limited thereto. For example, the medicinal solution may be a disinfection solution containing other than peracetic acid, or may be a detergent, a cleaning solution, or alcohol.

In the embodiment, the first guide roller 53, the second guide roller 54, and the engaging roller 55 are provided, but such rollers may be rod-shaped members that do not rotate.

In the embodiment, the medicinal solution supply mechanism 4 is connected to the medicinal solution tank 5 via the connection tube 6, but the present invention is not limited thereto. For example, the connection tube 6 may be connected to a cleaning reservoir of the endoscope reprocessor 1.

In the embodiment, the housing portion 11 includes the engaging groove 13a and the movable portion 51 includes the engaging roller 55, but the configuration relation may be reverse. Even in this case, when the housing portion 11 advances from the first point to the second point, the engaging roller enters the engaging groove through the engaging groove opening, and power to slide the movable portion 51 is transmitted to the engaging roller from the inner edge of the engaging groove.

The present invention is not limited to the embodiment described above, and various modifications and changes can be made without departing from the gist of the present invention.

What is claimed is:

1. An endoscope reprocessor comprising:
   a housing unit that houses a medicinal solution bottle such that a sealing portion is located on a top surface;
   a first guide that guides the housing unit such that the housing unit is capable of advancing and retreating between a first point and a second point;
   a movable unit that moves in cooperation with advancing of the housing unit;
   an unsealing member provided in the movable unit and arranged at a position higher than the sealing portion of the medicinal solution bottle housed in the housing unit at the first point, the unsealing member having a shape protruding toward the top surface at a predetermined length to pierce the sealing portion when the medicinal solution bottle reaches the second point by descending as the movable unit advances; and
   a second guide that guides an advancing direction of the movable unit.

2. The endoscope reprocessor according to claim 1, further comprising
   the medicinal solution bottle including the sealing portion on the top surface, wherein
   the sealing portion is arranged at a position where the unsealing member is mounted when the medicinal solution bottle is located at the second point.

3. The endoscope reprocessor according to claim 1, further comprising
   a main body, wherein
   the main body is coupled to the housing unit by the first guide and is coupled to the movable unit by the second guide, and
   the housing unit is arranged in the main body at the second point.

4. The endoscope reprocessor according to claim 1, wherein
   the housing unit includes an engaging groove including an engaging groove opening at a position of a first height on the main body,
   the movable unit includes an engaging roller arranged at a position of the first height at the first point and arranged at a position of a second height lower than the first height at the second point, and
   the engaging roller enters the engaging groove from the engaging groove opening when the housing unit advances from the first point to the second point, and power to slide the movable unit is transmitted to the engaging roller from an inner edge of the engaging groove.

5. The endoscope reprocessor according to claim 3, wherein
   the second guide includes guide plates inclined to approach the main body in a direction toward the main body from the housing unit.

6. The endoscope reprocessor according to claim 5, wherein
   the guide plates are arranged parallel to each other.

7. The endoscope reprocessor according to claim 6, wherein
- each of the guide plates includes two guide holes that support the movable unit, and
- the two guide holes are arranged parallel to each other in extending directions of the guide plates.

8. The endoscope reprocessor according to claim 1, wherein
- the housing unit includes an engaging roller at a position of a first height,
- the movable unit includes an engaging groove arranged at a position of the first height at the first point, arranged at a position of a second height lower than the first height at the second point, and including an engaging groove opening opened toward the housing unit, and
- the engaging roller enters the engaging groove from the engaging groove opening when the housing unit advances from the first point to the second point, and power to slide the movable unit is transmitted to the engaging roller from an inner edge of the engaging groove.

9. The endoscope reprocessor according to claim 1, wherein
- a height difference in descent of the unsealing member is smaller than a moving distance of the housing unit.

* * * * *